(12) United States Patent
Shio et al.

(10) Patent No.: US 8,168,157 B2
(45) Date of Patent: *May 1, 2012

(54) PRODUCTION METHOD OF FINE PARTICLE ZINC OXIDE POWDER AND COSMETICS CONTAINING THE SAME

(75) Inventors: Shoichiro Shio, Yokohama (JP); Atsushi Nakahira, Kyoto (JP); Hideaki Murase, Yao (JP)

(73) Assignee: Shiseido Company Ltd., Chuo-ku, Tokyo (JP)

( * ) Notice: Subject to any disclaimer, the term of this patent is extended or adjusted under 35 U.S.C. 154(b) by 148 days.

This patent is subject to a terminal disclaimer.

(21) Appl. No.: 12/515,567

(22) PCT Filed: Nov. 22, 2007

(86) PCT No.: PCT/JP2007/072668
§ 371 (c)(1), (2), (4) Date: May 20, 2009

(87) PCT Pub. No.: WO2008/062871
PCT Pub. Date: May 29, 2008

(65) Prior Publication Data
US 2010/0074837 A1    Mar. 25, 2010

(30) Foreign Application Priority Data
Nov. 22, 2006 (JP) .................. 2006-315273

(51) Int. Cl.
C01G 9/00 (2006.01)
(52) U.S. Cl. ........................................ 423/622
(58) Field of Classification Search ............... 423/622, 423/101, 102, 104; 424/641, 642, 401
See application file for complete search history.

(56) References Cited

U.S. PATENT DOCUMENTS

| | | | |
|---|---|---|---|
| 5,093,099 A | 3/1992 | Haishi et al. | |
| 5,527,519 A | 6/1996 | Miksits et al. | |
| 2005/0260122 A1 | 11/2005 | Li et al. | |
| 2009/0010971 A1* | 1/2009 | Shio et al. | 424/401 |

FOREIGN PATENT DOCUMENTS

| | | |
|---|---|---|
| EP | 0317272 | 5/1989 |
| JP | 1-230431 | 11/1987 |
| JP | 1-230431 | 9/1989 |
| JP | 4-357114 | 12/1992 |
| JP | 6-115937 | 4/1994 |
| JP | 7-291615 | 11/1995 |
| JP | 2002-284527 | 10/2002 |
| JP | 2004-142999 | 5/2004 |
| JP | 2004-204403 | * 7/2004 |
| JP | 2007-008804 | * 1/2007 |
| JP | 2007-8805 | 1/2007 |
| WO | 2006/129793 | * 12/2006 |

OTHER PUBLICATIONS

Patent Abstract for Japanese Publication No. 04-357114 published Dec. 10, 1992, one page.
Patent Abstract for Japanese Publication No. 06-115937 published Apr. 26, 1994, ten pages.
Patent Abstract for Japanese Publication No. 07-291615 published Nov. 7, 1995, 15 pages.
Patent Abstract for Japanese Publication No. 2002-284527 published Oct. 3, 2002, seven pages.
Patent Abstract for Japanese Publication No. 2004-142999 published May 20, 2004, seven pages.
Patent Abstract for Japanese Publication No. 2007-008805 published Jan. 18, 2007, 17 pages.
International Preliminary Report on Patentability for corresponding PCT/JP2007/072668 mailed Jun. 4, 2009, seven pages.
International Search Report for corresponding PCT/JP2007/072668 mailed Dec. 18, 2007, four pages.
Japanese Patent Abstract for Publication No. 01-230431 published Sep. 13, 1989, 1 page.
Japanese Patent Abstract for Publication No. 04-357114 published Dec. 10, 1992, one page.
Supplementary European Search Report for EP 07832397 mailed Mar. 12, 2010, 7 pages.

* cited by examiner

Primary Examiner — Steven Bos
(74) Attorney, Agent, or Firm — Rankin, Hill & Clark LLP

(57) ABSTRACT

It is to provide a production method of zinc oxide powder excellent in UV protection ability and transparency and to provide cosmetics containing the same. The fine particle zinc oxide powder is produced by subjecting either an aqueous solution containing both a water-soluble zinc salt and a carboxylic acid or an aqueous solution containing a water-soluble zinc carboxylate to pH adjustment with an alkali carbonate agent and aging the resulting mixture without calcining. The alkali carbonate agent may be 0.1 to 2 mol/L aqueous solution and the carboxylate group is 1 to 5 times in moles with respect to zinc. The pH adjustment can be carried out by dropwise addition of the alkali carbonate aqueous solution at 0.5 to 5 mL/min per 100 mL of either the aqueous solution containing both the water-soluble zinc salt and the carboxylic acid or the aqueous solution containing the water-soluble zinc carboxylate.

16 Claims, 5 Drawing Sheets

PRODUCTION METHOD OF FINE PARTICLE ZINC OXIDE POWDER AND COSMETICS CONTAINING THE SAME

RELATED APPLICATIONS

This application claims the priority of Japanese Patent Application No. 2006-315273 filed on Nov. 22, 2006, which is incorporated herein by reference.

FIELD OF THE INVENTION

The present invention relates to a production method of zinc oxide powder, and in particular, relates to a production method of fine particle zinc oxide powder that can achieve excellent UV protection ability and transparency.

BACKGROUND OF THE INVENTION

In the past, the achievement of transparency was pursued for the zinc oxide that is used as a UV protection agent in cosmetics. As a result, ultrafine particle powder with an average particle size of 100 nm or less has been mainly used.

The production of zinc oxide is mainly classified into a dry process and a wet process. As for the dry processes, these include the French process (indirect method) and the American process (direct method); in these processes, zinc oxide is produced by the oxidation of zinc vapor by air. The dry process is the main method for the production of ordinary zinc oxide. However, the wet process has been mainly used for the production of UV-shielding ultrafine particulate zinc oxide with a particle size of 100 nm or less.

The wet process is a method in which an aqueous solution of a zinc salt is neutralized with an alkaline agent, and the formed precipitate of zinc salt is washed with water, dried, and calcined to obtain zinc oxide. Generally, sodium carbonate is used as an alkaline agent to adjust the pH, and then the formed hydrozincite is decarboxylated by calcination at 300 to 500° C., thereby producing zinc oxide. Usually, zinc oxide produced by such a production method is called low-temperature calcined zinc oxide.

However, this method has a problem in that the formed fine particles of 100 nm or less aggregate due to sintering during calcination. As a result, the particle size increases, and the transparency and UV shielding property are undermined.

In order to suppress sintering of fine particles, zinc oxide whose particles are beforehand formed to various shapes has been proposed. For example, flaky zinc oxide powder is described in patent literature 1 and patent literature 2.

If the flaky powder is thin, however, the powder strength is not sufficient during the manufacturing of products such as cosmetics. If the thickness is increased to increase the strength, the particle size of the powder becomes too large, and an issue such as the scattering of visible light leading to a decrease in transparency arises in actual usage.

In patent literature 3, fine particle zinc oxide is supported inside the pores of porous spherical silica. However, when the zinc oxide with effective particle sizes for UV protection is supported, the amount supported will be too small. If the supported amount is increased, the smaller zinc oxide than the zinc oxide with effective particle sizes for UV protection will be supported; as a result, the effective UV protection ability cannot be achieved. When a large amount of sufficiently large zinc oxide is supported, the particle size of carrier silica will become too large; as a result, the efficiency of UV protection will become poor.

Other various approaches have also been tried, but they were hardly satisfactory.

Thus far, there is no reported synthesis method, of fine particle zinc oxide from zinc carbonate, wherein no calcining step is involved in order to prevent aggregation.

Patent Literature 1 Unexamined Japanese Patent Publication No. H01-230431
Patent Literature 2: Unexamined Japanese Patent Publication No. H06-115937
Patent Literature 1: Unexamined Japanese Patent Publication No. H07-291615

DISCLOSURE OF THE INVENTION

Problem to be Solved by the Invention

The present invention was made in view of the above-described problems of the background art, and the object is to provide a production method of zinc oxide powder excellent in UV protection ability and transparency and to provide cosmetics containing the same.

Means to Solve the Problem

The present inventors have diligently studied to accomplish the above-described task. As a result, the present inventors have found that fine particle zinc oxide powder of uniform particle sizes can be obtained, without a calcining step, by a specific production method. It has also been found that this zinc oxide powder can achieve excellent UV protection ability (especially UV-A protection ability) and visible light transmission (transparency), thus leading to completion of the present invention.

That is, the production method of fine particle zinc oxide powder of the present invention is characterized by comprising steps of:
  subjecting either an aqueous solution containing both a water-soluble zinc salt and a carboxylic acid or an aqueous solution containing a water-soluble zinc carboxylate to pH adjustment with an alkali carbonate agent; and
  aging the resulting mixture without calcining to produce fine particle zinc oxide powder.

In the method of the present invention, it is preferable that the alkali carbonate agent is 0.1 to 2 mol/L aqueous solution per 100 mL of either the aqueous solution containing both the water-soluble zinc salt and the carboxylic acid or the aqueous solution containing the water-soluble zinc carboxylate.

It is preferable that the carboxylate group in either the aqueous solution containing both the water-soluble zinc salt and the carboxylic acid or the aqueous solution containing the water-soluble zinc carboxylate is 1 to 5 times in moles with respect to zinc therein.

It is preferable that the pH adjustment is carried out by dropwise addition of the alkali carbonate aqueous solution at 0.5 to 5 mL/min per 100 mL of either the aqueous solution containing both the water-soluble zinc salt and the carboxylic acid or the aqueous solution containing the water-soluble zinc carboxylate.

In the method of the present invention, it is preferable that: the alkali carbonate aqueous solution is dropwise added to either the aqueous solution containing both the water-soluble zinc salt and the carboxylic acid or the aqueous solution containing the water-soluble zinc carboxylate; the pH adjustment is terminated by stopping the dropwise addition of the alkali carbonate aqueous solution at a point when a second pH drop is observed in temporal pH change of the resulting mixture during the dropwise addition; and then the aging is carried out.

It is preferable that the water-soluble zinc salt is zinc chloride.

It is preferable that the carboxylic acid is acetic acid.

It is preferable that the water-soluble zinc carboxylate is zinc acetate.

It is preferable that the alkali carbonate agent is sodium carbonate or sodium hydrogencarbonate.

A cosmetic of the present invention is characterized by comprising the fine particle zinc oxide powder produced by any of the above-described methods.

Effect of the Invention

The production method of fine particle zinc oxide powder of the present invention is characterized in that the decarboxylation is conducted through a pH adjustment step and not through a calcination step. Thus, the aggregation of particles due to sintering is suppressed, and fine particle zinc oxide that can achieve excellent UV protection ability (especially UV-A protection ability) and visible light transmission (transparency) can be obtained. In addition, the cost reduction can be achieved because the equipment involved in calcining is not necessary.

BEST MODE FOR CARRYING OUT THE INVENTION

Figure 1:
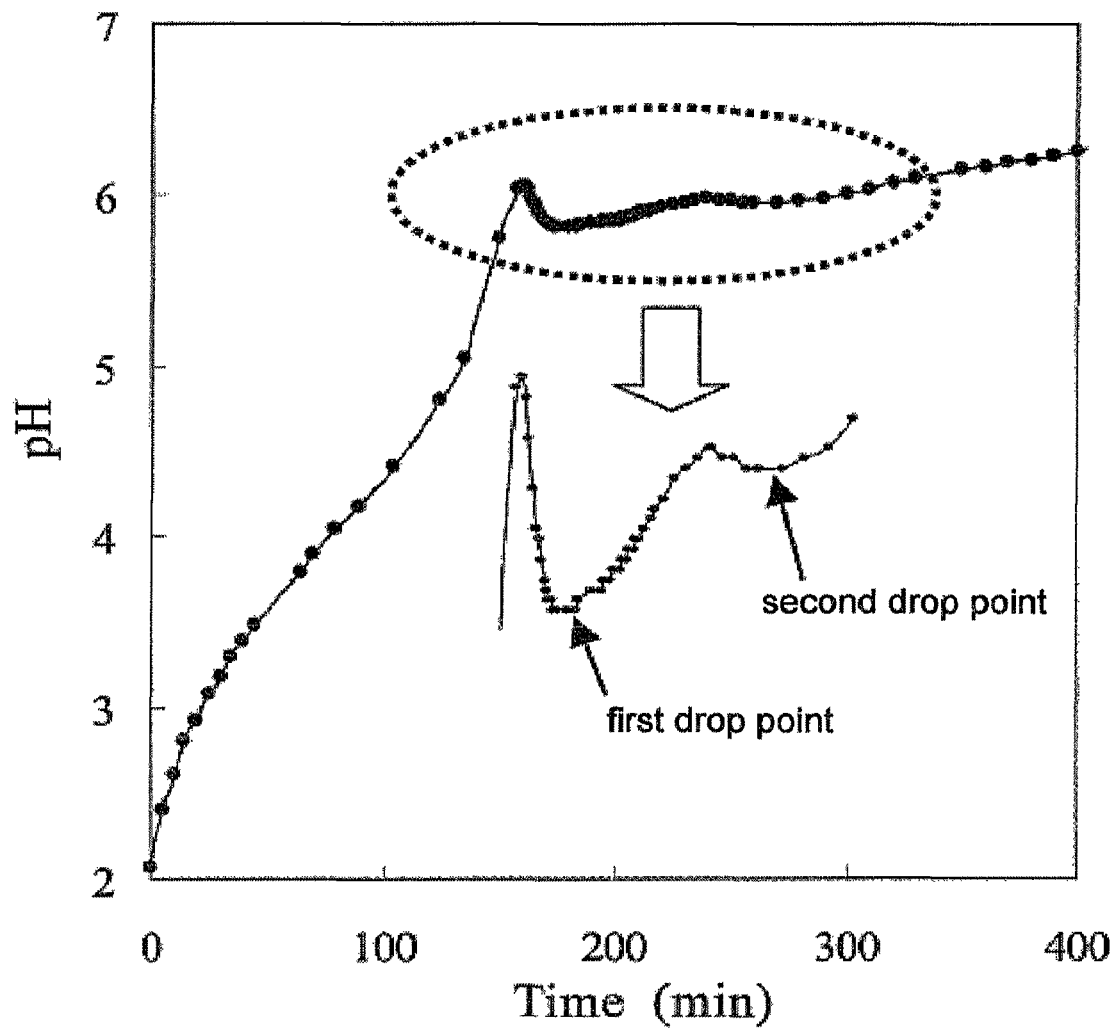
FIG. 1 shows a relationship between the pH of the reaction solution and the reaction time from the start of the dropwise addition of sodium carbonate aqueous solution to the completion of aging in the production process of the fine particle zinc oxide powder (Test Example 1), which is one example of the present invention.

The fine particle zinc oxide powder of the present invention can be obtained by neutralizing either an aqueous solution containing both a water-soluble zinc salt and a carboxylic acid or an aqueous solution containing a water-soluble zinc carboxylate (hereinafter, these aqueous solutions may be called "zinc aqueous solutions") by the addition, at 40° C. or lower, of an alkaline agent having carbonate group (alkali carbonate agent), aging, washing with water, and drying. In the aqueous solution containing a water-soluble zinc carboxylate, the additional carboxylic acid may be used. The UV protection ability and transparency tend to be better in the case in which the aqueous solution containing both the water-soluble zinc salt and the carboxylic acid are used than the case in which the water-soluble zinc carboxylate aqueous solution is used; thus the former is more preferable.

As the water-soluble zinc salt, those normally used in the liquid phase method can be listed. Examples include zinc chloride, zinc nitrate, zinc sulfate, and zinc acetate; among them zinc chloride or zinc acetate is preferable, and zinc chloride is especially preferable. When a water-soluble zinc carboxylate is used as the water-soluble zinc salt, the addition of a carboxylic acid may be omitted.

As the carboxylic acid used with a water-soluble zinc salt, a water-soluble carboxylic acid can be used. Examples include formic acid, acetic acid, propionic acid, oxalic acid, citric acid, tartaric acid, succinic acid, and maleic anhydride; among them, acetic acid is preferable.

The water-soluble zinc carboxylate is a water-soluble zinc salt of the above-described carboxylic acids; among them, zinc acetate is preferable.

As the alkali carbonate agent, water-soluble carbonate salts such as sodium carbonate, potassium carbonate, sodium hydrogencarbonate, and potassium hydrogencarbonate can be suitably used; among them, sodium carbonate or sodium hydrogencarbonate is preferable.

The concentration of the water-soluble zinc salt or zinc carboxylate in the zinc aqueous solution is normally 0.1 to 5 mol/L at the start of the reaction.

A carboxylic acid used with a water-soluble zinc salt is 1 to 5 times in moles, as the carboxylate group, with respect to zinc, and preferably 1 to 3 times in moles. If the amount of the carboxylic acid is too small or too large, the decarboxylation of hydrozincite to zinc oxide by aging tends to be unsatisfactory.

When other carboxylic acids are used instead of acetic acid, the decarboxylation by aging also takes place. However, when a mineral acid or the like is used, the decarboxylation does not take place; as a result, zinc oxide cannot be obtained. Therefore, in order to obtain zinc oxide by decarboxylation of hydrozincite in the reaction process, the coexistence of zinc ions and carboxylate ions is considered to be necessary when the neutralization with an alkali carbonate agent is being carried out.

In order to achieve complete dissolution of the zinc aqueous solution, however, an additional mineral acid may also be used. Examples of mineral acids include hydrochloric acid, nitric acid, and sulfuric acid; among them, hydrochloric acid can be preferably used.

When the above-described zinc aqueous solution is neutralized with an alkali carbonate agent, it is preferable to continuously add the alkali carbonate aqueous solution while the zinc aqueous solution is being stirred.

The concentration of the alkali carbonate aqueous solution is preferably 0.1 to 2 mol/L, and more preferably 0.2 to 0.8 mol/L.

In addition, it is preferable that the rate of dropwise addition of the alkali carbonate aqueous solution is 0.5 to 5 mL/min per 100 mL of the zinc aqueous solution.

If the concentration of alkali carbonate agent or the rate of dropwise addition is too small, the reaction takes a longer time and is inefficient. On the other hand, if the concentration of the alkali carbonate agent or the rate of dropwise addition is too large, the decarboxylation may not take place, and the functionality of powder may also be affected.

Instead of sodium carbonate, sodium hydrogencarbonate or other alkaline agents having carbonate group may be used; fine particle zinc oxide powder can similarly be obtained by aging. When other alkaline agents, such as sodium hydroxide, having no carbonate group are used instead of an alkali carbonate agent, zinc oxide cannot be obtained by aging. Thus, it is considered necessary to form hydrozincite by the neutralization with carbonate ions.

When an alkali carbonate aqueous solution is dropwise added to a zinc aqueous solution, a zinc salt starts to precipitate at a certain addition amount. In the case where a solution containing zinc chloride and acetic acid is neutralized with a sodium carbonate aqueous solution, the pH of the reaction solution at the precipitation starting point is normally 5.5 to 6.5. Up to the precipitation starting point, the pH increases with an increase in the addition amount. After the start of precipitation, however, the pH increase with the progress of addition is generally very mild because sodium carbonate is consumed for the precipitation of the zinc salt. Immediately after the start of precipitation and afterward, points of temporary pH drop are observed, respectively. In the present invention, the former may be called the first pH drop point, and the latter may be called the second pH drop point. After the completion of zinc salt precipitation, which is past the second pH drop point, the pH rapidly increases.

In the present invention, the dropwise addition of sodium carbonate is terminated at the second pH drop point (point at which the second pH downward phenomenon takes place). The precipitate at this point is hydrozincite. After the termination of dropwise addition, the stirring is continued to carry out aging until hydrozincite is converted to zinc oxide. The stirring time (aging time) varies depending upon the zinc concentration in the reaction; normally it is 1 to 10 hours, and more preferably 5 to 10 hours. If the aging time is short, the conversion rate of hydrozincite to zinc oxide will be low. If the aging time is too long, it will be a waste of time because further conversion does not take place.

If the dropwise addition is terminated at the first drop point or the dropwise addition is terminated after passing the second drop point, it will be difficult to obtain zinc oxide only by aging and without calcining.

It is preferable to carry out the reaction of the above-described zinc aqueous solution and the alkali carbonate aqueous solution at 40° C. or lower. If the reaction temperature exceeds 40° C., the formation of fine particles is hindered and the satisfactory functionality may not be achieved. If the reaction temperature is too low, problems such as the decreased efficiency in precipitation formation and the precipitation or freezing of the raw materials take place. Therefore, the reaction temperature should normally be 15° C. or higher, and preferably 25° C. or higher. It is also preferable to carry out the aging in this temperature range.

After aging, the obtained precipitate is separated from the liquid, as necessary, by a publicly known method such as filtration or centrifugation, and the solid phase is washed with water and then dried. Although natural drying, reduced-pressure drying, or freeze-drying is possible, the drying is normally carried out at 80 to 120° C. for about 1 to 24 hours.

In the thus obtained fine particle zinc oxide powder, the average particle size of the primary particles is normally about 0.01 to 0.1 μm. The particle size was measured by electron microscope observation.

The fine particle zinc oxide powder obtained in the present invention can achieve high UV protection ability (especially UV-A protection ability) and visible light transmission.

That is, the fine particle zinc oxide powder of the present invention is microscopic; thus the transmittance in the UV light region is low, and the transmittance in the visible light region is high. As a result, a high UV protection ability and visible-light transmission can be achieved. As described later, for example, in a 5% castor oil dispersion of the fine particle zinc oxide powder of the present invention, the transmittance at 360 nm can be made to 20% or lower and further to 15% or lower, and the transmittance at 450 nm can be made to 85% or higher and further to 90% or higher.

With the use of the fine particle zinc oxide powder of the present invention, cosmetics containing the fine particle zinc oxide powder can be produced.

The amount of the fine particle zinc oxide powder blended in cosmetics is suitably determined depending on the purpose. The amount blended in cosmetics is normally 0.001 mass % or higher, and preferably 1 mass % or higher. If the amount is too small, the effect cannot be achieved. On the other hand, the upper limit is not restricted in particular. Even when a large amount is blended, excess whiteness is not caused on the skin and the usability is good. However, considering other components to be blended, the blending quantity is normally 50 mass % or lower, and preferably 30 mass % or lower.

For the fine particle zinc oxide powder of the present invention, a publicly known surface treatment may be applied as necessary. Examples include treatments with: fatty acid soaps such as aluminum stearate and zinc myristate; waxes such as candelilla wax and carnauba wax; silicones such as methyl polysiloxane and cyclic silicone oils; dextrin fatty acid esters such as dextrin palmitate; fatty acids such as myristic acid and stearic acid; and fluoride.

In the cosmetics, other components that are normally blended in cosmetics can be blended in addition to the fine particle zinc oxide powder. Examples include oils, moisturizers, surfactants, pigments, dyes, powder, antioxidants, preservatives, pH adjusters, chelating agents, perfumes, UV absorbers, whitening agents, water, and various drugs.

The cosmetics of the present invention can be provided in any form such as a powder form, solid form, ointment form, liquid form, emulsion form, or a solid-liquid separated form.

Examples of product forms include basic cosmetics such as lotion, milky lotion, and cream; makeup cosmetics such as foundation, pre-makeup, lipstick, eye shadow, cheek color, eye liner, nail enamel, and mascara; and hair cosmetics such as hair treatment, hair cream, hair liquid, and setting lotion. The blending of the fine particle zinc oxide powder of the present invention is especially effective in sunscreen cosmetics for UV protection.

In addition to cosmetics, the fine particle zinc oxide powder of the present invention is applicable to other applications for UV protection. Examples include resin compositions, paint, ink, and coating compositions; however, the applications are not limited to these.

EXAMPLES

Test Example 1

Production of Fine Particle Zinc Oxide Powder

To 100 mL of 1 mol/L zinc chloride aqueous solution in a flask, 100 mL of 1 mol/L acetic acid aqueous solution was added and dissolved. To this solution under stirring, 0.2 mol/L sodium carbonate aqueous solution was dropwise added at a rate of 1.5 mL/min at 25° C. The pH during the reaction was monitored over time. At the point when the second pH drop was observed (dropwise addition time of about 270 minutes), the dropwise addition was terminated, but the stirring was continued for 360 minutes to carry out aging. The temporal pH change from the start of the addition of the sodium carbonate aqueous solution to the completion of aging is shown in FIG. 1.

Then, the obtained precipitate was filtered, washed with water, and then dried (105° C., 12 hours) to obtain the powder of "Test Example 1".

Figure 2:
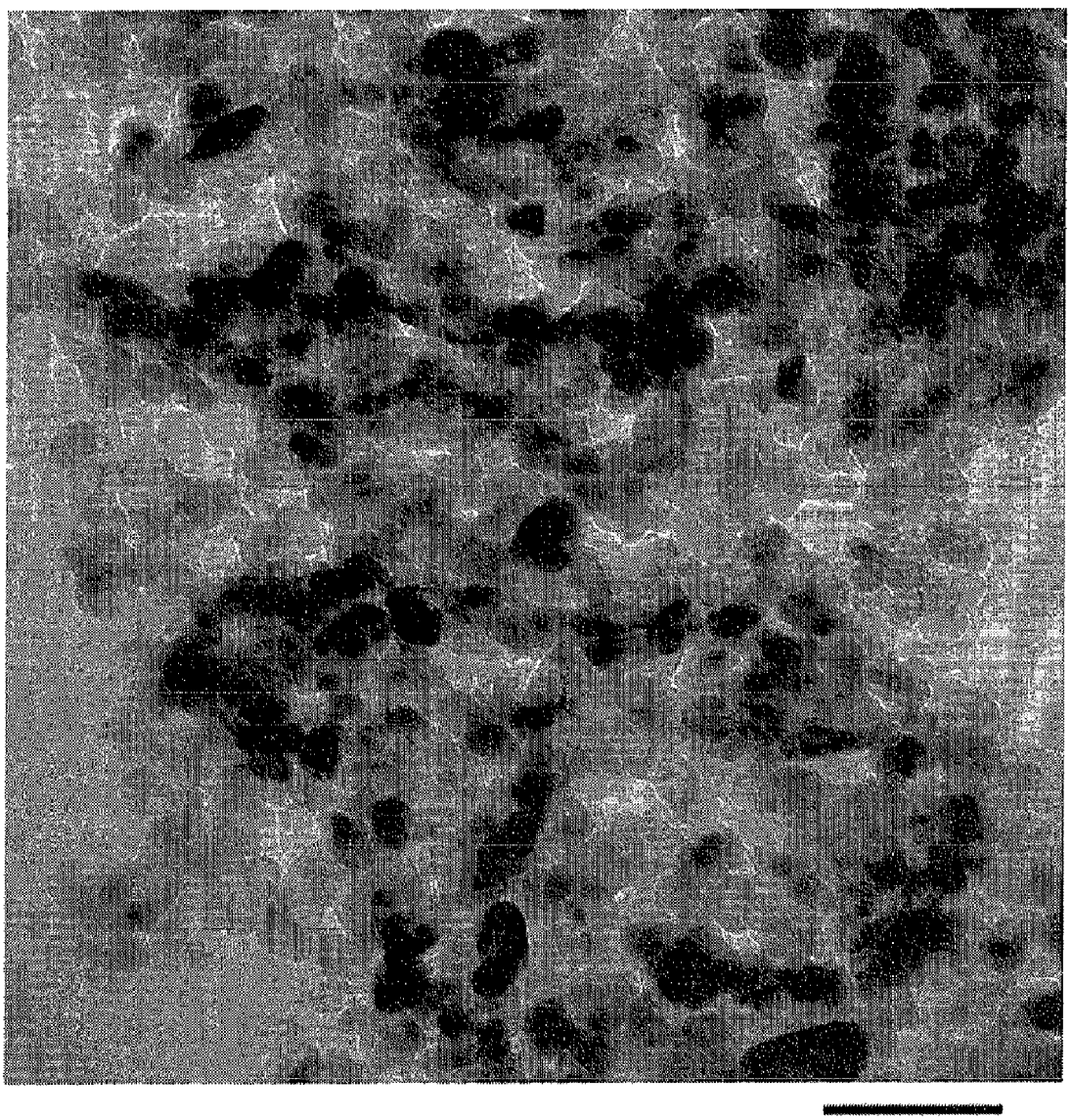
FIG. 2 is a TEM micrograph of the fine particle zinc oxide powder (Test Example 1), which is one example of the present invention.

The obtained powder was confirmed to be zinc oxide from the results of X-ray diffraction. This powder was observed with a transmission electron microscope (TEM). As shown in FIG. 2, microscopic particles were formed and the particle size was about 20 nm.

In addition, 2 g of zinc oxide powder of "Test Example 1" was sufficiently grinded and dispersed, with a three-roller mill, in 3 g of castor oil. The obtained dispersion was further diluted with castor oil to a powder concentration of 5 mass %. At a film thickness of 5 μm, the transmittance from 280 to 700 nm was measured. For comparison, the castor oil dispersion of a commercial ultra-fine particle zinc oxide powder (manufactured by Tayca Corporation, MZ-500, particle size: 20 to 30 nm) was measured in the same way. The results are shown in FIG. 3.

Figure 3:
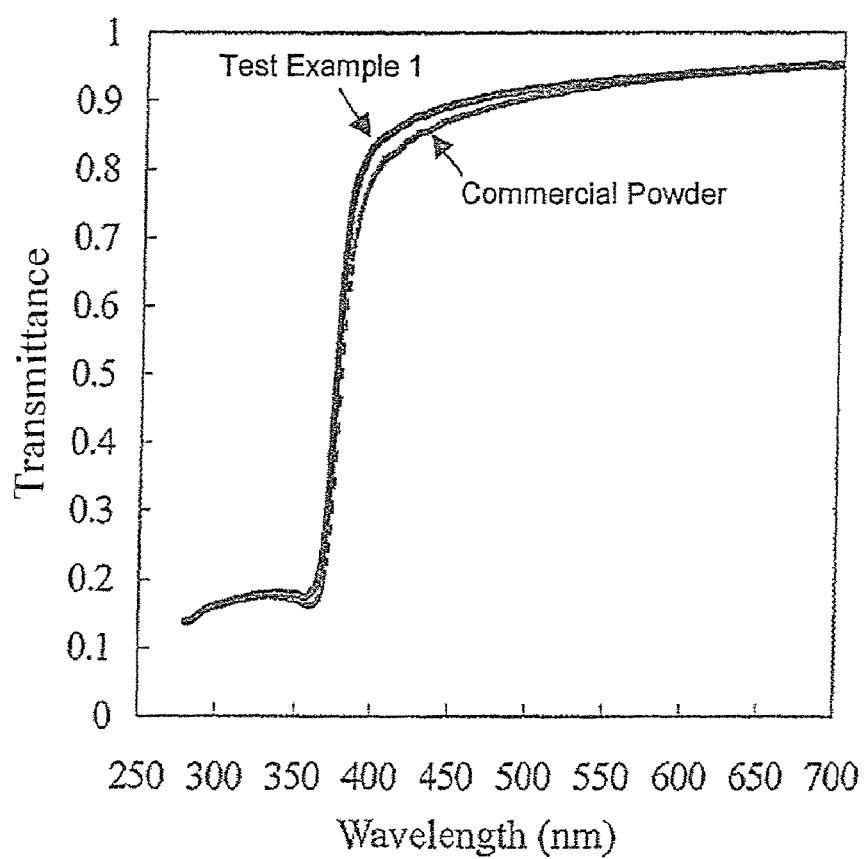
FIG. 3 shows spectral transmittance curves of the fine particle zinc oxide powder (Test Example 1), which is one example of the present invention and a commercial ultra-fine particle zinc oxide powder.

As shown in FIG. 3, "Test Example 1" achieved a higher visible light transmission than the conventional ultra-fine particle zinc oxide powder. The transmittance in the visible region (for example, 450 nm) was 90% or higher, and that in the UV region (for example, 360 nm) was 20% or lower.

Test Example 2

Effect of Aging Time

Figure 4:
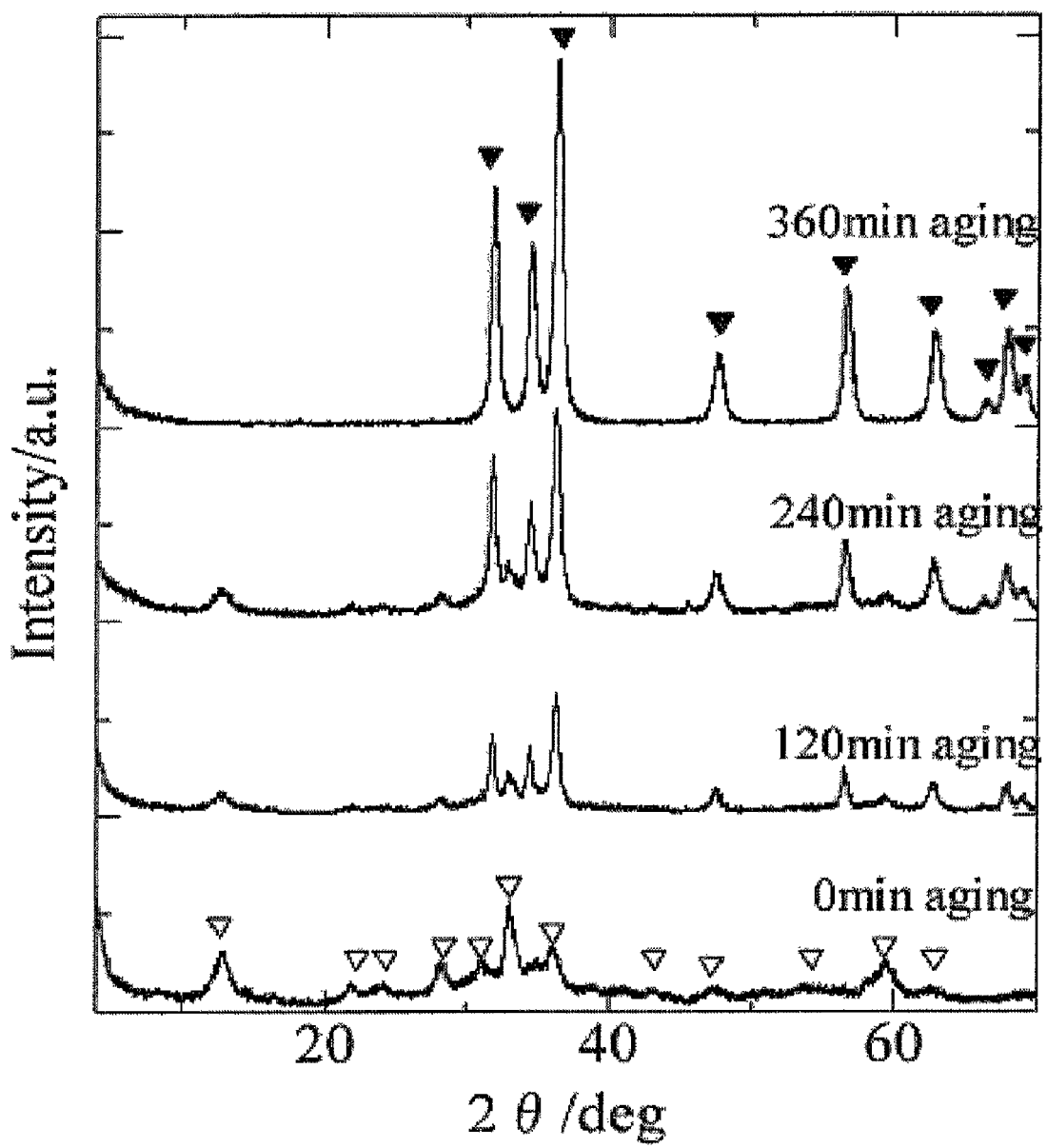
FIG. 4 shows X-ray diffraction patterns for the powders obtained by varying the aging time in the production process of the fine particle zinc oxide powder (Test Example 1), which is one example of the present invention.

Powders were obtained, in the same way as "Test Example 1", by varying the aging time. The conversion to zinc oxide was investigated by X-ray diffraction (FIG. 4). The relationship between the aging time and the products are shown in Table 1.

TABLE 1

| Test Example No. | Aging Time(min.) | Product |
| --- | --- | --- |
| 2-1 | 0 | hydrozincite |
| 2-2 | 120 | hydrozincite, zinc oxide |
| 2-3 | 240 | hydrozincite, zinc oxide |
| 1 | 360 | zinc oxide |

The powder obtained immediately after the termination of the dropwise addition of sodium carbonate (Test Example 2-1, without aging) was 100% hydrozincite. When the aging time was 120 minutes (Test Example 2-2) or 240 minutes (Test Example 2-3), a mixture of hydrozincite and zinc oxide was obtained. By 360 minute aging (Test Example 1), a powder of 100% zinc oxide was obtained.

Thus, it is understood that the conversion of hydrozincite to zinc oxide progresses with the elapse of the aging time.

Although the detailed mechanism is unknown at present, it seems that zinc oxide is formed by the decarboxylation, due to aging, of hydrozincite.

Test Example 3

Effect of Termination Point of Dropwise Addition (Aging Initiation Point)

The powder was obtained in the same way as "Test Example 1" except that the termination point of dropwise addition of sodium carbonate was varied. The conversion to zinc oxide was observed by X-ray diffraction, and the results are shown in Table 2.

TABLE 2

| Test Example No. | Termination of Sodium Carbonate Addition | Product |
| --- | --- | --- |
| 3-1 | 1st pH drop point | hydrozincite |
| 1 | 2nd pH drop point | zinc oxide |
| 3-2 | pH 8 | hydrozincite |

When a sodium carbonate aqueous solution was dropwise added under the conditions of Test Example 1, the pH increased with time, as shown in FIG. 1, and the formation of a precipitate and the first pH drop were observed at a dropwise addition time of about 170 minutes. By further dropwise addition, the pH gradually increased, and the second pH drop was observed at a dropwise addition time of about 270 minutes. By further dropwise addition, the pH gradually increased again. When the dropwise addition time exceeded about 470 minutes, the pH rapidly increased. At a dropwise addition time of about 500 minutes, the pH reached 8.

The dropwise addition of sodium carbonate was terminated at the observation of the first pH drop or at pH 8. Then, the aging (25° C., 360 minutes) was carried out, respectively. In both cases the obtained powder was hydrozincite.

Because the mechanism of decarboxylation is unknown, detailed analysis cannot be performed. However, it seems that there is an optimum hydrozincite crystal structure for the conversion of hydrozincite to zinc oxide.

Test Example 4

Amount of Carboxylic Acid

The powder was obtained in the same way as "Test Example 1" except that the amount of used acetic acid was varied. The conversion to zinc oxide was investigated by X-ray diffraction, and the results are shown in Table 3.

As shown in Table 3, both when the amount of used acetic acid was too small and when it was too large, the conversion efficiency of hydrozincite to zinc oxide was poor.

Thus, in the conversion of hydrozincite to zinc oxide, the suitable amount of carboxylic acid is 1 to 5 times in moles with respect to the amount of zinc, and the preferable amount is 1 to 3 times in moles.

TABLE 3

| Amount with respect to Zn (times in moles) | Product |
| --- | --- |
| 0 | hydrozincite |
| 0.2 | hydrozincite |
| 1.0 | zinc oxide |
| 3.0 | zinc oxide |
| 5.0 | hydrozincite, zinc oxide |

Test Example 5

Concentration of Alkali Carbonate Agent

The powder was obtained in the same way as "Test Example 1" except that the concentration of sodium carbonate aqueous solution was varied. The conversion to zinc oxide was investigated by X-ray diffraction, and the results are shown in Table 4.

TABLE 4

| Concentration of Sodium Carbonate aq. sol.* (mol/L) | Product |
| --- | --- |
| 0.05 | hydrozincite |
| 0.2 | zinc oxide |
| 0.5 | zinc oxide |
| 1.0 | hydrozincite, zinc oxide |
| 2.0 | hydrozincite, zinc oxide |

*Rate of dropwise addition of the sodium carbonate aqueous solution: 1.5 mL/min

As shown in Table 4, when the concentration of sodium carbonate aqueous solution was increased while keeping a constant rate of dropwise addition, the conversion efficiency of hydrozincite to zinc oxide became poor. On the other hand, when the concentration was lowered too much, the conversion to zinc oxide did not take place.

Thus, the concentration of alkali carbonate aqueous solution is preferably 0.1 to 2 mol/L, and more preferably 0.2 to 0.8 mol/L.

Test Example 6

Rate of Dropwise Addition of Alkali Carbonate Agent

The powder was obtained in the same way as "Test Example 1" except that the rate of dropwise addition of the sodium carbonate aqueous solution was varied. The conversion to zinc oxide was investigated by X-ray diffraction, and the results are shown in Table 5.

TABLE 5

| Rate of dropwise addition of Sodium Carbonate aq. sol.* (mL/min) | Product |
| --- | --- |
| 1.5 | zinc oxide |
| 5.0 | hydrozincite, zinc oxide |
| 10.0 | hydrozincite, zinc oxide |

*Concentration of the sodium carbonate aqueous solution: 0.2 mol/L

As shown in Table 5, when the rate of dropwise addition was increased while keeping a constant concentration of the sodium carbonate aqueous solution, the conversion efficiency of hydrozincite to zinc oxide became poor. On the other hand, if the rate of dropwise addition is too low, the reaction time becomes significantly longer and it is not efficient.

Thus, for the formation of zinc oxide, the preferable rate of dropwise addition of the alkali carbonate aqueous solution is 0.5 to 5 mL/min per 100 mL of the zinc aqueous solution, and more preferably 0.5 to 4.0 mL/min.

Test Example 7

Production of Fine Particle Zinc Oxide

To 100 mL of 1 mol/L zinc chloride aqueous solution in a flask, 100 mL of 1 mol/L acetic acid aqueous solution was added and dissolved. To this solution under stirring, 0.2 mol/L sodium hydrogencarbonate aqueous solution was dropwise added at a rate of 1.5 mL/min at 25° C. The pH during the reaction was monitored over time. At the point when the second pH drop was observed (dropwise addition time of about 500 minutes), the dropwise addition was terminated, but the stirring was continued for 360 minutes to carry out aging.

Then, the obtained precipitate was filtered, washed with water, and then dried (105° C., 12 hours) to obtain the powder of "Test Example 7". X-ray diffraction patterns after the termination of dropwise addition and after aging are shown in FIG. 5.

Figure 5:
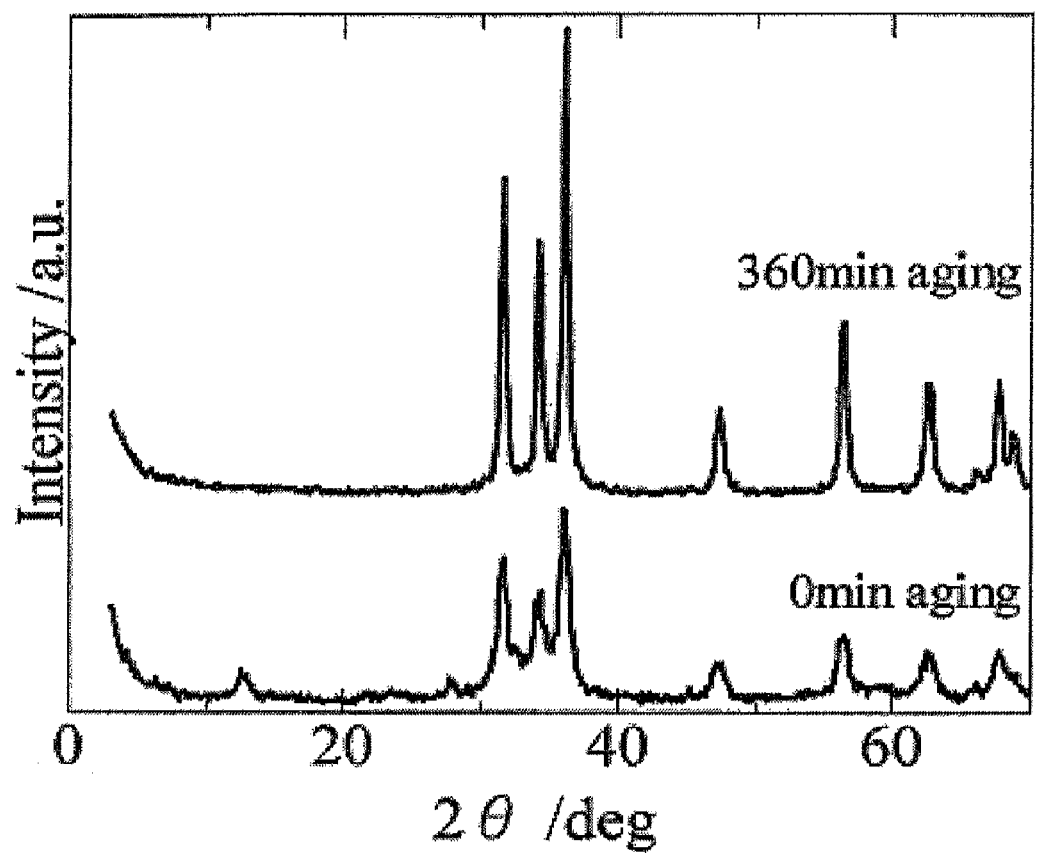
FIG. 5 shows X-ray diffraction patterns for the powder at the point of the termination of dropwise addition and for the powder after aging in the production process of the fine particle zinc oxide powder (Test Example 7), which is one example of the present invention.

According to FIG. 5, zinc oxide is formed even immediately after the termination of dropwise addition. Thus, the use of sodium hydrogencarbonate as the alkaline agent is more effective than the use of sodium carbonate for the conversion to zinc oxide.

| Composition Example 1 O/W Milky Lotion | |
| --- | --- |
| (Water Phase) | |
| Purified water | to 100 mass % |
| Dipropylene glycol | 6.0 |
| Ethanol | 3.0 |
| Hydroxyethyl cellulose | 0.3 |
| Fine particle zinc oxide powder | 5.0 |
| (Oil Phase) | |
| Octyl p-methoxycinnamate | 6.0 |
| Glyceryl octyl p-methoxycinnamate | 2.0 |
| 4-tert-Butyl-4'-methoxydibenzoylmethane | 2.0 |
| Oxybenzone | 3.0 |
| Oleyl oleate | 5.0 |
| Dimethylpolysiloxane | 3.0 |
| Petrolatum | 0.5 |
| Cetyl alcohol | 1.0 |
| Sorbitan sesquioleate | 0.8 |
| POE (20) oleyl alcohol | 1.2 |
| Antioxidant | Q.S. |
| Antiseptic | Q.S. |
| Perfume | Q.S. |

| Composition Example 2 W/O Cream | |
| --- | --- |
| (Water Phase) | |
| Purified water | to 100 mass % |
| 1,3-Butylene glycol | 10.0 |
| (Oil Phase) | |
| Fine particle zinc oxide powder (hydrophobized) | 20.0 |
| Squalane | 20.0 |
| Glyceryl diisostearate | 5.0 |
| Organophilic montmorillonite | 3.0 |
| Antiseptic | Q.S. |
| Perfume | Q.S. |

| Composition Example 3 Sunscreen Oil | |
| --- | --- |
| Fine particle zinc oxide powder (hydrophobized) | 10.0 mass % |
| Liquid paraffin | 48.0 |
| Isopropyl myristate | 10.0 |
| Silicone oil | 30.0 |
| Silicone resin | 2.0 |
| Antioxidant | Q.S. |
| Perfume | Q.S. |

Composition Example 4
Gel

| | |
|---|---|
| Fine particle zinc oxide powder | 10.0 mass % |
| Liquid paraffin | 65.0 |
| Olive oil | 20.0 |
| Organophilic montmorillonite | 5.0 |
| Antioxidant | Q.S. |
| Perfume | Q.S. |

Composition Example 5
Dual-use Foundation

| | |
|---|---|
| Silicone-treated talc | 19.2 mass % |
| Silicone-treated mica | 40.0 |
| Fine particle zinc oxide powder (hydrophobized) | 5.0 |
| Silicone-treated titanium dioxide | 15.0 |
| Silicone-treated red iron oxide | 1.0 |
| Silicone-treated yellow iron oxide | 3.0 |
| Silicone-treated black iron oxide | 0.2 |
| Zinc stearate | 0.1 |
| Nylon powder | 2.0 |
| Squalane | 4.0 |
| Solid paraffin | 0.5 |
| Dimethylpolysiloxane | 4.0 |
| Glyceryl triisooctanoate | 5.0 |
| Octyl methoxycinnamate | 1.0 |
| Antiseptic | Q.S. |
| Antioxidant | Q.S. |
| Perfume | Q.S. |

Composition Example 6
O/W Liquid Foundation

| | |
|---|---|
| Talc | 3.0 mass % |
| Fine particle zinc oxide powder | 15.0 |
| Red iron oxide | 0.5 |
| Yellow iron oxide | 1.4 |
| Black iron oxide | 0.1 |
| Bentonite | 0.5 |
| POE sorbitan monostearate | 0.9 |
| Triethanolamine | 1.0 |
| Propylene glycol | 10.0 |
| Purified water | to 100 |
| Stearic acid | 2.2 |
| Isohexadecyl alcohol | 7.0 |
| Glyceryl monostearate | 2.0 |
| Liquid lanolin | 2.0 |
| Liquid paraffin | 2.0 |
| Antiseptic | Q.S. |
| Perfume | Q.S. |

Composition Example 7
W/O Foundation (two-layer type)

| | |
|---|---|
| Hydrophobized talc | 7.0 mass % |
| Fine particle zinc oxide powder (hydrophobized) | 12.0 |
| Silicic anhydride | 2.0 |
| Nylon powder | 4.0 |
| Color pigment | 2.0 |
| Octamethylcyclotetrasiloxane | 10.0 |
| Pentaerythritol rosinate | 1.5 |
| Neopentyl glycol diisooctanoate | 5.0 |
| Squalane | 2.5 |
| Glyceryl triisooctanoate | 2.0 |
| Polyoxyethylene dimethylpolysiloxane | 1.5 |
| Purified water | to 100 |
| 1,3-Butylene glycol | 4.0 |
| Ethanol | 7.0 |

Composition Example 8
Powdery foundation

| | |
|---|---|
| Talc | 20.3 |
| Mica | 30.0 |
| Kaolin | 5.0 |
| Fine particle zinc oxide powder | 10.0 |
| Titanium dioxide | 5.0 |
| Zinc stearate | 1.0 |
| Red iron oxide | 1.0 |
| Yellow iron oxide | 3.0 |
| Black iron oxide | 0.2 |
| Nylon powder | 10.0 |
| Squalane | 6.0 |
| Lanolin acetate | 1.0 |
| Octyldodecyl myristate | 2.0 |
| Neopentyl glycol diisooctanoate | 2.0 |
| Sorbitan monooleate | 0.5 |
| Antiseptic | Q.S. |
| Perfume | Q.S. |

The cosmetics of the above-described composition examples were prepared by the conventional method. In all cosmetics, there was no problem in the product appearance and product stability. When applied on the skin, they did not cause white masking and achieved high UV protection ability (especially UV-A protection ability).

What is claimed is:

1. A production method of fine particle zinc oxide powder comprising steps of:
   dropwise adding an alkali carbonate agent to either an aqueous solution containing both a water-soluble zinc salt and a carboxylic acid or an aqueous solution containing a water-soluble zinc carboxylate to adjust the pH of the mixture, wherein the pH adjustment is carried out by dropwise addition of the alkali carbonate aqueous solution at 0.5 to 5 mL/min per 100 mL of either the aqueous solution containing both the water-soluble zinc salt and the carboxylic acid or the aqueous solution containing the water-soluble zinc carboxylate; and
   aging the resulting mixture without calcining to produce fine particle zinc oxide powder.

2. The method according to claim 1, wherein the alkali carbonate agent is 0.1 to 2 mol/L aqueous solution per 100 mL of either the aqueous solution containing both the water-soluble zinc salt and the carboxylic acid or the aqueous solution containing the water-soluble zinc carboxylate.

3. The method according to claim 1 wherein the carboxylate group in either the aqueous solution containing both the water-soluble zinc salt and the carboxylic acid or the aqueous solution containing the water-soluble zinc carboxylate is 1 to 5 times in moles with respect to zinc therein.

4. The method of claim 1, wherein the alkali carbonate aqueous solution is dropwise added to either the aqueous solution containing both the water-soluble zinc salt and the carboxylic acid or the aqueous solution containing the water-soluble zinc carboxylate; the pH adjustment is terminated by stopping the dropwise addition of the alkali carbonate aqueous solution at a point when a second pH drop is observed in temporal pH change of the resulting mixture during the dropwise addition; and then the aging is carried out.

5. The method of claim 1, wherein the water-soluble zinc salt is zinc chloride.

6. The method of claim 1, wherein the carboxylic acid is acetic acid.

7. The method of claim 1, wherein the water-soluble zinc carboxylate is zinc acetate.

8. The method of claim 1, wherein the alkali carbonate agent is sodium carbonate or sodium hydrogencarbonate.

9. The method according to claim 2, wherein the carboxylate group in either the aqueous solution containing both the water-soluble zinc salt and the carboxylic acid or the aqueous solution containing the water-soluble zinc carboxylate is 1 to 5 times in moles with respect to zinc therein.

10. The method of claim 2, wherein the pH adjustment is carried out by dropwise addition of the alkali carbonate aqueous solution at 0.5 to 5 mL/min per 100 mL of either the aqueous solution containing both the water-soluble zinc salt and the carboxylic acid or the aqueous solution containing the water-soluble zinc carboxylate.

11. The method of claim 4, wherein the alkali carbonate agent is 0.1 to 2 mol/L aqueous solution per 100 mL of either the aqueous solution containing both the water-soluble zinc salt and the carboxylic acid or the aqueous solution containing the water-soluble zinc carboxylate.

12. The method of claim 4, wherein the carboxylate group in either the aqueous solution containing both the water-soluble zinc salt and the carboxylic acid or the aqueous solution containing the water-soluble zinc carboxylate is 1 to 5 times in moles with respect to zinc therein.

13. The method of claim 4, wherein the water-soluble zinc salt is zinc chloride.

14. The method of claim 4, wherein the carboxylic acid is acetic acid.

15. The method of claim 4, wherein the water-soluble zinc carboxylate is zinc acetate.

16. The method of claim 4, wherein the alkali carbonate agent is sodium carbonate or sodium hydrogencarbonate.

* * * * *